US007608438B2

(12) United States Patent
Laviolette

(10) Patent No.: US 7,608,438 B2
(45) Date of Patent: Oct. 27, 2009

(54) PROCESS FOR THE CONTINUOUS PRODUCTION OF ETHANOL

(76) Inventor: Jessica Laviolette, 1001 Oakwood Rd., Ortonville, MI (US) 48462

( * ) Notice: Subject to any disclaimer, the term of this patent is extended or adjusted under 35 U.S.C. 154(b) by 381 days.

(21) Appl. No.: 11/654,913

(22) Filed: Jan. 18, 2007

(65) Prior Publication Data

US 2007/0178568 A1 Aug. 2, 2007

Related U.S. Application Data

(63) Continuation-in-part of application No. 11/099,404, filed on Apr. 5, 2005, now abandoned.

(51) Int. Cl.
*C12O 7/06* (2006.01)

(52) U.S. Cl. ...................................................... 435/161

(58) Field of Classification Search ....................... None
See application file for complete search history.

(56) References Cited

U.S. PATENT DOCUMENTS

| | | | |
|---|---|---|---|
| 4,326,036 A | 4/1982 | Hayes | |
| 4,567,145 A | 1/1986 | Faber et al. | |
| 4,778,688 A | 10/1988 | Matson | |
| 4,816,407 A | 3/1989 | Matson | |
| 4,822,737 A | 4/1989 | Saida | |
| 4,996,073 A | 2/1991 | Copeland et al. | |
| 5,362,501 A | 11/1994 | Gopeland et al. | |
| 5,432,083 A | 7/1995 | Copeland et al. | |
| 5,554,520 A | 9/1996 | Fowler et al. | |
| 6,861,248 B2 | 3/2005 | Dale et al. | |
| 7,070,967 B2 | 7/2006 | Dale et al. | |
| 7,122,709 B2 | 10/2006 | Fanselow et al. | |
| 7,374,905 B2 * | 5/2008 | Copeland et al. | 435/34 |
| 2003/0104608 A1 | 6/2003 | Copeland et al. | |
| 2003/0153059 A1 | 8/2003 | Pilkington et al. | |
| 2005/0170483 A1 | 8/2005 | Elnashaie et al. | |
| 2007/0031954 A1 | 2/2007 | Mairal et al. | |
| 2007/0178568 A1 | 8/2007 | Laviolette | |
| 2007/0249029 A1 | 10/2007 | Marshall et al. | |
| 2008/0057553 A1 | 3/2008 | Cadwalader | |
| 2008/0176303 A1 | 7/2008 | Massie | |
| 2008/0207959 A1 | 8/2008 | Plante et al. | |
| 2008/0213848 A1 | 9/2008 | Gaddy et al. | |
| 2008/0229653 A1 | 9/2008 | Iversen et al. | |
| 2009/0017512 A1 | 1/2009 | May et al. | |

FOREIGN PATENT DOCUMENTS

| | | |
|---|---|---|
| EP | 195094 | 9/1986 |
| FR | 2616354 | 12/1988 |
| JP | 58094388 | 6/1983 |
| JP | 62250907 | 10/1987 |
| JP | 63222681 | 9/1988 |
| JP | 7322884 | 12/1995 |
| JP | 2006043576 | 2/2006 |
| WO | 9400589 | 1/1994 |
| WO | 9521932 | 8/1995 |
| WO | 9637627 | 11/1996 |

OTHER PUBLICATIONS

International Search Report and Written Opinion dated May 19, 2008, PCT/US2008/051251.

* cited by examiner

*Primary Examiner*—Herbert J. Lilling
(74) *Attorney, Agent, or Firm*—Carlson, Gaskey & Olds

(57) ABSTRACT

A process for the production of ethanol utilizes a vacuum process and selectively permeable membranes to increase ethanol production efficiency. Yeast converts sugars to ethanol in an anaerobic condition within process chamber void of oxygen and filled with a Nitrogen gas (N2) or any non-oxygen containing gas. A glucose solution is fed into the process chamber to a yeast solution to ferment. A selectively permeable membrane filters ethanol away from the yeast and out of the process chamber. The removal of ethanol from the process chamber keeps the yeast alive to constantly produce ethanol.

11 Claims, 3 Drawing Sheets

10
28
18
30
$N_2$
Vacuum
16
20
12
14
$P_1$
26
32
32
32
$P_2$
24
22

32
34
24
35
40
P1
P2
35
24

PROCESS FOR THE CONTINUOUS PRODUCTION OF ETHANOL

CROSS REFERENCE TO RELATED APPLICATION

This application is a continuation in part of U.S. patent application Ser. No 11/099,404 which was filed on Apr. 5, 2005, now abandoned.

BACKGROUND OF THE INVENTION

This invention relates generally to the field of renewable fuel productions and more specifically to a process for the production of ethanol by use of a vacuum process and selectively permeable membranes to increase ethanol production efficiency.

Production of ethanol is an age old technology that has lacked development throughout the centuries. In both traditional ethanol production (wine making, etc) and commercial ethanol production yeast, a facultative anaerobe, is placed in a solution of sugar or fermenting mash that is open in some way to oxygen. The yeast is allowed to ferment the sugars (glucose) into ethanol until the concentration of ethanol to fermenting mash reaches approximately 15%, at which, the enzyme in the yeast that converts sugar to ethanol is destroyed or denatured due to the high concentration of ethanol and hence ceasing ethanol production. Ethanol production is both more time consuming and only partially efficient.

To overcome some obstacles in ethanol production, such as random strains of bacteria ruining the ethanol production process, traditional and commercial ethanol producers sanitize all the equipment used in ethanol production in some way (usually through the use of an iodine solution) to ensure that ethanol and not vinegar will be produced. This has helped to improve the efficiency of ethanol production. Ethanol production ceases once the concentration of ethanol to fermenting mash reaches approximately 15%. To overcome this barrier, some producers have experimented with different strains of yeast or genetically altered yeast to produce high tolerance yeast that can continue to produce ethanol until the concentration of ethanol to fermenting mash reaches approximately 18% to 20%. Basically, the yeast that produces ethanol has a higher tolerance to ethanol concentrations and will not denature until a concentration of approximately 18% to 20% has been reached but this form of improvement (yeast being tolerant to ethanol) is limited.

Deficiencies in prior technology include the presence of oxygen in the fermenting mash, either at the surface of the mash or dissolved within the mash, and the fact that the yeast is directly exposed to the fermenting mash. When yeast has oxygen available to it, it will go through cellular respiration rather than alcoholic fermentation, hence making ATP (adenosine triphosphate) instead of ethanol.

Accordingly, it is desirable to design and develop new methods and systems for increasing the efficiency in the ethanol producing process.

SUMMARY OF THE INVENTION

An example method and system increases the efficiency of ethanol production by removing oxygen from contact with ethanol producing yeast, and by continuously removing ethanol through a selectively permeable membrane.

An example system utilizes a vacuum process to eliminate oxygen in the fermenting mash to ensure that fermenting mash is not exposed to oxygen during fermentation. This provides for the constant production of ethanol because the yeast is a facultative anaerobe.

By eliminating all forms of oxygen, the yeast is forced to constantly go through alcoholic fermentation, hence constantly producing ethanol. This allows the efficiency rate of ethanol production to be greatly improved. A selectively permeable membrane is utilized to maintain a maximum concentration of ethanol with basic yeast of approximately 15% and with genetically engineered yeast of approximately 18-20%. The yeast is suspended within the selectively permeable membrane such that the ethanol and perhaps small amounts of the fermenting yeast pass through the membrane while keeping the yeast inside the membrane with a fresh supply of fermenting mash (glucose solution). This allows the concentration of ethanol to fermenting mash to stay below 15% and allow for constant ethanol production without denaturing the yeast.

Accordingly, an example system and method provides for improved efficiency in the production of ethanol.

These and other features of the present invention can be best understood from the following specification and drawings, the following of which is a brief description.

DETAILED DESCRIPTION OF THE PREFERRED EMBODIMENT

Figure 1:
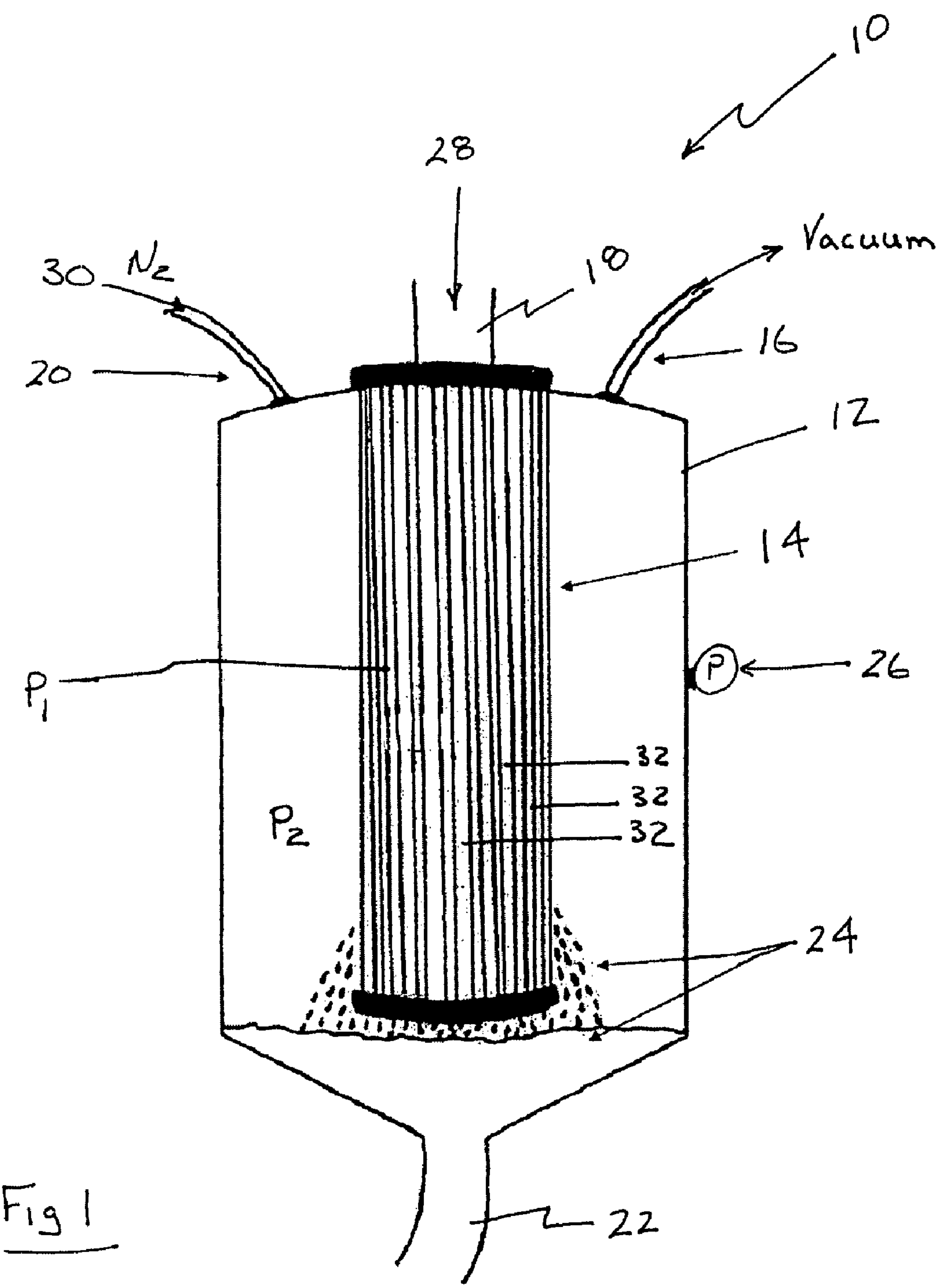
FIG. 1 is a schematic view of an example device for producing ethanol.

Referring to FIG. 1, an example ethanol producing device 10 includes a fermenting chamber 12 that is void of oxygen and filled with a non-oxygen containing gas. Air within the fermenting chamber 12 is removed through a vacuum line 16 and Nitrogen gas (N2) 30 is fed into the fermenting chamber 12 through a hose 20.

A bundle 14 of tubes 32 is disposed within the fermenting chamber 12. Each of the tubes 32 are fabricated from a selectively permeable membrane that allows ethanol 24 to migrate through the tubes 14 and into the fermenting chamber 12 where it is exhausted through the outlet 22.

The example process for the production of ethanol utilizes a pressure differential between a pressure P1 within the tubes 32, and a pressure P2 within the fermentation chamber 12 to draw ethanol 24 through the selectively permeable membrane of the tubes 32 and into the fermentation chamber 12.

The example process includes the initial step of introducing a biologically pure yeast culture into each of the tubes 14. The fermentation chamber 12 is sealed from ambient air and oxygen and is filled with a non-oxygen containing gas such as for example Nitrogen 30. Because the fermentation chamber 12 is substantially void of oxygen, the yeast culture maintains alcoholic fermentation of the glucose solution 28. In the presence of oxygen, the yeast culture will undergo a cellular respiration and produces ATP (adenosine triphosphate) instead of the desired ethanol.

The fermentation chamber can begin with a non-oxygen containing gas such as Nitrogen 30. Alternatively, a vacuum applied through the vacuum hose 16 can first remove any oxygen or air to provide for replacement with the desired non-oxygen containing gas. Oxygen removal is accomplished with a vacuum pumping system as is known. Other methods of removing oxygen from the fermentation chamber 12 in preparation for filling with a non-oxygen containing gas are also within the contemplation of this invention.

Once the fermentation chamber 12 is devoid of substantially all oxygen, the glucose solution 28 is fed into the bundle 14 of tubes 32. Each of the tubes 32 includes a desired amount of yeast that goes through an alcoholic fermentation in combination with the introduced glucose solution 28. The non-oxygen atmosphere within the fermentation chamber 12 ensures that the yeast and glucose solution will undergo alcoholic fermentation to produce ethanol.

The glucose solution 28 is fed into the tubes 32 within the fermentation chamber 12 at a rate determined to provide a desired production of ethanol. The fermentation chamber 12 includes the inlet 18 for the glucose solution 28 and the outlet 22 for the ethanol 24 produced. The tubes 32 are made from a selectively permeable membrane that provides for the evacuation of ethanol, while maintaining the yeast and glucose solution within the tubes 14.

Figure 2:
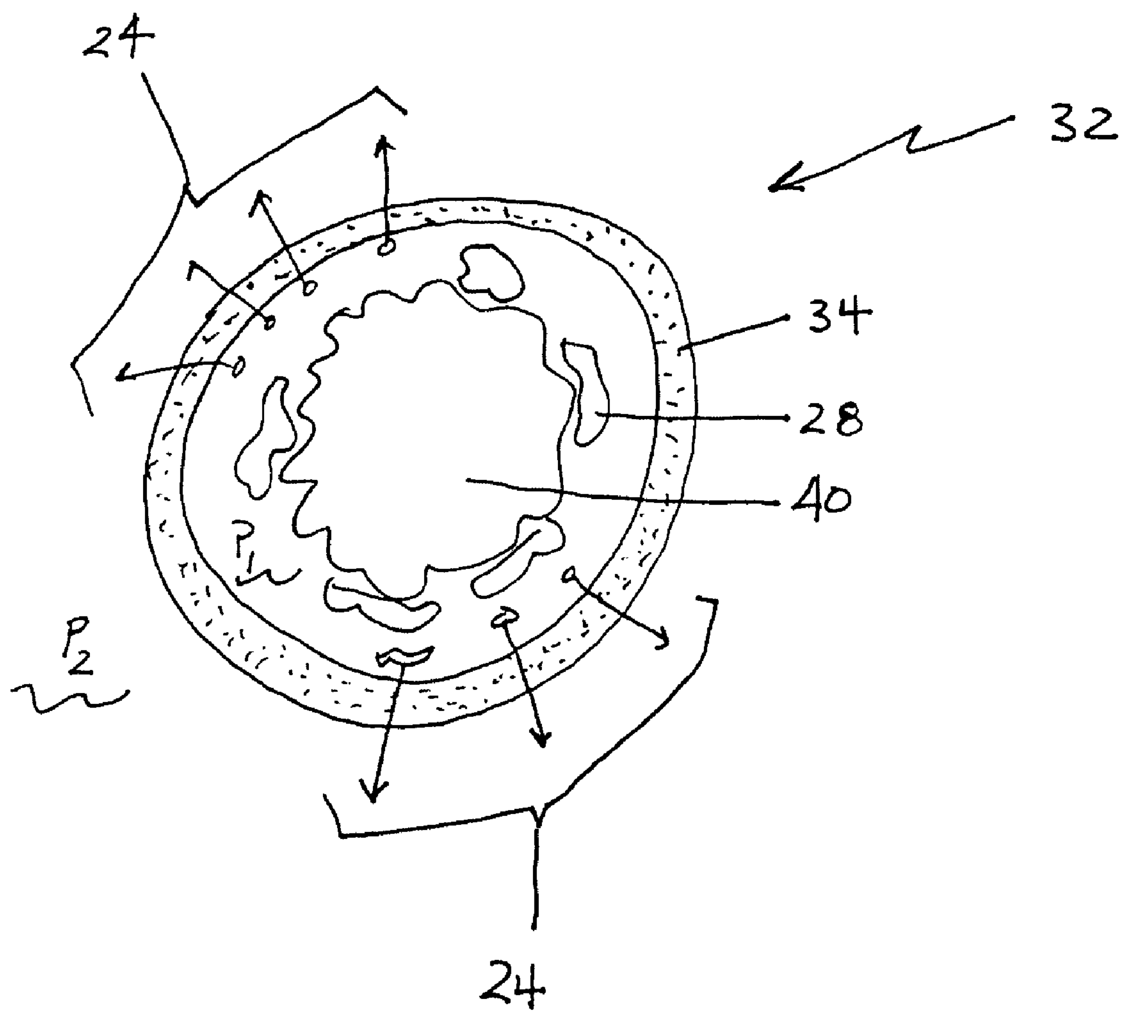
FIG. 2 is an enlarged schematic view of an example tube of the example device.
Figure 3:
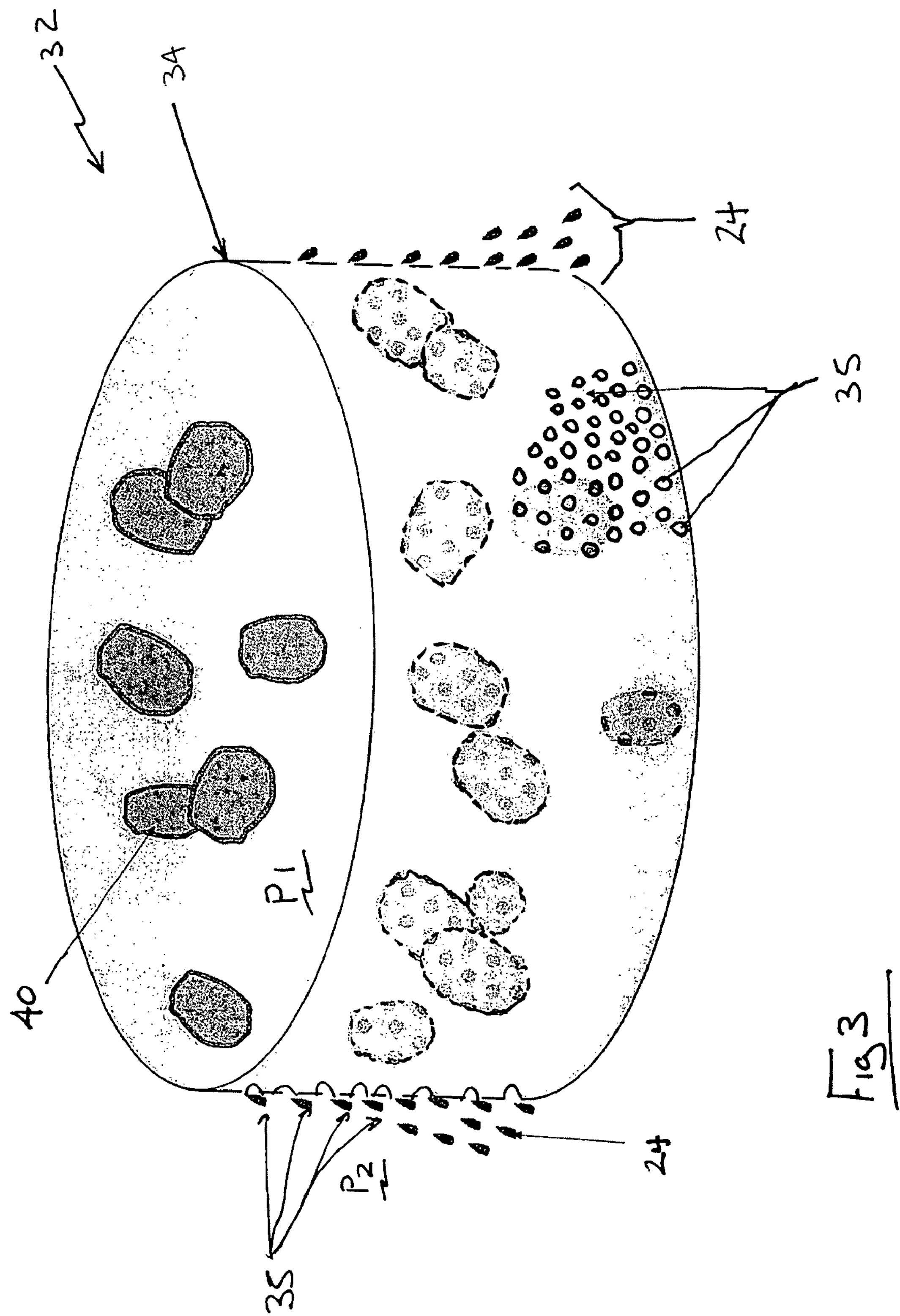
FIG. 3 is another enlarged schematic view of an example tube of the example device.

Referring to FIGS. 2 and 3, the tube 32 includes a wall fabricated of a selectively permeable membrane 34. The selectively permeable membrane 34 if of material compatible with the environment within the fabrication chamber 12. Further, the selectively permeable membrane 34 is of a defined porosity that allows Ethanol to pass through, but that does not allow other elements such as the yeast 40 to pass through. The porosity is a function of the open area that allows ethanol evacuation for a give area. The example tube 32 includes a number of pores 35 (FIG. 3) disposed over the surface area of the tube 32. The number and size of pores 35 are determined based on the size of the specific yeast utilized in fermentation process. The permeable membrane 34 prevents the evacuation of the yeasts 40 and glucose solutions 28 to maintain the desired production of ethanol 24. Selectively permeable membranes are known devices and are available for allowing desired content and elements through while retaining the desired elements and compounds within the chamber.

Referring back to FIG. 1, with continued reference to FIGS. 2 and 3, during the alcoholic fermentation process, the inside of the tube 32 begins to become filled with ethanol 24. A desired percentage of ethanol 24 within the tube relative to the amount of yeast 40 is controlled by controlling the flow of ethanol 24 through the selectively permeable membrane 34. The flow of ethanol through the selectively permeable membrane 34 is controlled by controlling a pressure differential between P1 and P2 across the permeable membrane 34. Control of the pressure differential across the permeable membrane 34 along with the specific porosity of the permeable membrane 34 relative to the yeast 40 and glucose solution 28 utilized for the example process provide for a substantially continuous process where glucose 28 is fed in and ethanol 24 is forced through the selectively permeable membrane 34. Accordingly, the desired flow of ethanol from the plurality of tubes 14 is controlled and continuous.

The percent of ethanol 24 to yeast 40 is maintained at a rate determined to not cause the denaturing of the yeast 40. As appreciated, yeasts of different purities perform most efficiently ad different ethanol concentrations. For example, alcoholic fermentation for normal yeasts begins to degrade as the ethanol concentration approaches 15% relative to the amount of yeasts. Some genetically engineered yeast provides efficient ethanol production up approaching 18-20% ethanol relative to the amount of yeast contained within the process chamber. The system and method of this invention maintains the desired ratio of yeast to ethanol by evacuating ethanol through the selectively permeable membrane 34. Accordingly, the process can continue for as long as glucose solution is fed into the bundle of tubes 14.

The yeast 40 is suspended within the tubes 14 of the fermentation chamber 12 and does not move through the selectively permeable membrane 34. The selectively permeable membrane 34 is selected from commercially available devices according to the specific yeast and glucose utilized for the fermentation process. A worked skilled in the art would understand that selectively permeable membranes of differing capabilities can be utilized for different conditions created by different yeast types and glucose types. Further, as the selectively permeable membrane 34 allows ethanol 24 to pass therethrough, and not a substantial portion of the other contents within the tube 32, the selectively permeable membrane 34 selected will always provide for a desired amount of ethanol 24 to diffuse therethrough responsive to a pressure differential determined to provide the driving force for exhausting a desired amount of ethanol from the tube 32 that would provide a desired balance within each of the tubes 32.

A fresh supply of glucose solution 28, also known in the art as "fermenting mash" is continually introduced into the tubes 32 as required to maintain the desired rate of ethanol production that corresponds to the desired concentration of ethanol within the fermentation chamber 12.

The glucose solution 28 flows through the tube 32 in contact with the yeast 40. Circulation of the glucose solution 28 provides for reuse of the solution to efficiently utilize any glucose that did not undergo the fermentation process.

While the invention has been described in connection with a preferred embodiment, it is not intended to limit the scope of the invention to the particular form set forth, but on the contrary, it is intended to cover such alternatives, modification, and equivalents as may be included within the spirit and scope of the invention as defined by the appended claims.

Although a preferred embodiment of this invention has been disclosed, a worker of ordinary skill in this art would recognize that certain modifications would come within the scope of this invention. For that reason, the following claims should be studied to determine the true scope and content of this invention.

What is claimed is:

1. A method of continuously producing ethanol comprising the steps of:

a) creating an oxygen free environment within a closed process chamber;

b) supporting an ethanol producing yeast within the closed process chamber;

c) introducing a glucose solution into the process chamber for reaction with the ethanol producing yeast; and d) removing ethanol produced during fermentation from the process chamber through a selectively permeable membrane to control a concentration of ethanol within the process chamber; wherein the selectively permeable membrane provides for ethanol to flow therethrough, and prevents the flow of yeast therethrough and wherein the concentration of ethanol within the process chamber is controlled such that the concentration of ethanol does not exceed a concentration determined to denature the ethanol producing yeast.

2. The method as recited in claim 1, wherein step a comprises removing oxygen from the process chamber with a vacuum.

3. The method as recited in claim 1, wherein the selectively permeable membrane provides for the flow of at least some of the glucose solution out of the process chamber.

4. The method as recited in claim 1, including the step of controlling the flow of ethanol through the selectively permeable membrane to maintain a desired concentration of ethanol within the process chamber.

5. The method as recited in claim 1, wherein step c includes controlling the flow of the glucose solution into the process chamber for controlling alcoholic fermentation.

6. The method as recited in claim 1, wherein the selectively permeable membrane includes a plurality of pores.

7. The method as recited in claim 1, wherein step a comprises filling the process chamber with a non-oxygen containing gas.

8. The method as recited in claim 7, wherein the non-oxygen containing gas comprises Nitrogen gas.

9. The method as recited in claim 1, wherein step c includes flowing glucose solution into the process chamber, and out of the process chamber through the selectively permeable membrane.

10. The method as recited in claim 1, including the step of maintaining the ethanol producing yeast within the process chamber.

11. The method as recited in claim 1, wherein the concentration of ethanol within the process chamber is controlled such that the concentration of ethanol to the ethanol producing yeast does not exceed 20%.

* * * * *